United States Patent
Sithian (10) Patent No.: US 8,475,513 B2
(45) Date of Patent: Jul. 2, 2013

(54) STENT GRAFT APPARATUS AND METHOD

(76) Inventor: Nedunchezian Sithian, Staten Island, NY (US)

(*) Notice: Subject to any disclaimer, the term of this patent is extended or adjusted under 35 U.S.C. 154(b) by 735 days.

(21) Appl. No.: 12/629,436

(22) Filed: Dec. 2, 2009

(65) Prior Publication Data

US 2011/0130828 A1 Jun. 2, 2011

(51) Int. Cl.
*A61F 2/06* (2006.01)

(52) U.S. Cl.
USPC .......................................... 623/1.11; 623/1.35

(58) Field of Classification Search
USPC .................................. 623/1.35, 1.11
See application file for complete search history.

(56) References Cited

U.S. PATENT DOCUMENTS

| | | | | |
|---|---|---|---|---|
| 5,575,817 A * | 11/1996 | Martin | | 623/1.35 |
| 5,824,036 A * | 10/1998 | Lauterjung | | 623/1.11 |
| 5,824,042 A * | 10/1998 | Lombardi et al. | | 623/1.13 |
| 5,824,055 A * | 10/1998 | Spiridigliozzi et al. | | 623/1.11 |
| 6,203,568 B1 * | 3/2001 | Lombardi et al. | | 623/1.13 |
| 6,368,345 B1 * | 4/2002 | Dehdashtian et al. | | 623/1.13 |
| 6,368,355 B1 * | 4/2002 | Uflacker | | 623/23.7 |
| 6,375,675 B2 * | 4/2002 | Dehdashtian et al. | | 623/1.13 |
| 6,428,565 B1 | 8/2002 | Wisselink | | |
| 6,440,161 B1 * | 8/2002 | Madrid et al. | | 623/1.11 |
| 6,451,053 B1 * | 9/2002 | Dehdashtian et al. | | 623/1.34 |
| 6,576,007 B2 * | 6/2003 | Dehdashtian et al. | | 623/1.13 |
| 6,641,606 B2 * | 11/2003 | Ouriel et al. | | 623/1.12 |
| 6,682,537 B2 * | 1/2004 | Ouriel et al. | | 606/108 |
| 6,689,157 B2 * | 2/2004 | Madrid et al. | | 623/1.11 |
| 7,235,083 B1 | 6/2007 | Perez et al. | | |
| 7,320,703 B2 | 1/2008 | DiMatteo et al. | | |
| 7,537,606 B2 | 5/2009 | Hartley et al. | | |
| 7,594,926 B2 | 9/2009 | Linder et al. | | |
| 8,206,427 B1 * | 6/2012 | Ryan et al. | | 623/1.11 |
| 8,236,040 B2 * | 8/2012 | Mayberry et al. | | 623/1.11 |
| 2002/0173835 A1 * | 11/2002 | Bourang et al. | | 623/1.11 |
| 2004/0243221 A1 | 12/2004 | Fawzi et al. | | |
| 2006/0009833 A1 | 1/2006 | Chobotov et al. | | |
| 2007/0010781 A1 | 1/2007 | Vijay | | |
| 2008/0208309 A1 | 8/2008 | Saeed | | |
| 2008/0255656 A1 | 10/2008 | Saeed | | |
| 2008/0288045 A1 | 11/2008 | Saeed | | |
| 2009/0132026 A1 | 5/2009 | Martin et al. | | |
| 2011/0130828 A1 * | 6/2011 | Sithian | | 623/1.23 |

FOREIGN PATENT DOCUMENTS

WO    WO2008/103463 A2    8/2008

OTHER PUBLICATIONS

The AneuRx® Stent Graft System, Patient Information Booklet, Medtronic AVE, AAA Overview for Patients, 2002.

* cited by examiner

*Primary Examiner* — Darwin Erezo
(74) *Attorney, Agent, or Firm* — Gordon & Jacobson, PC (57) ABSTRACT

An apparatus and associated surgical method for repairing abdominal aortic aneurysms is disclosed. The apparatus includes first and second stent grafts made from a metal form structure in combination with a flexible fabric, and a flexible guidewire detachably attached to the first stent graft. The first stent graft has an upper tubular body which defines an inlet, and a lower bifurcation which includes a first tubular leg defining a first outlet, and a second tubular leg defining a second outlet. The method includes advancing the first stent graft through one iliac artery and deploying it in the aorta, advancing a guidewire engagement device distally through the other iliac artery and pulling the flexible guidewire into the other iliac artery, advancing a guide catheter over the flexible guidewire into the second tubular leg of the first stent graft, replacing the flexible guide wire with a stiffer guide wire through the guide catheter, and advancing a catheter delivery system provided with a second stent graft over the stiffer guide wire into the second tubular leg of the first stent graft.

7 Claims, 9 Drawing Sheets

STENT GRAFT APPARATUS AND METHOD

BACKGROUND OF THE INVENTION

1. Field of the Invention

This invention relates broadly to implant devices and methods used in the abdominal aorta. More particularly, this invention relates to repair devices and methods for treating abdominal aortic aneurysms.

2. State of the Art

When a blood vessel such as a vein or an artery deteriorates and/or suffers trauma, such deterioration and/or trauma may impair the blood vessel's ability to carry blood, and often creates a high risk of rupture due to the weakened blood vessel's inability to withstand internal pressures caused by blood flow and normal flexing and compression of the blood vessel. Impaired blood flow and/or a high risk of rupture may be life threatening to a patient, particularly when the weakened blood vessel is an important (e.g. large) vein or artery. For example, the main artery in a human body is the aorta, which supplies blood to all of the body's organs except the lungs. The aorta is generally described with reference to three different portions—the ascending aorta, which rises upward from the left ventricle of the heart, the aortic arch, which arches downward from the ascending aorta, and the descending aorta, which extends downward from the aortic arch through the thorax and the abdomen. The descending aorta divides into two iliac arteries which supply blood to the pelvis and lower extremities. Deterioration or trauma to the aorta may cause abnormal dilation of the wall of the aorta as it passes through the abdomen, a condition which is called an abdominal aortic aneurysm. This type of aneurysm ordinarily occurs in the portion of the aorta below the kidneys, and if left untreated, will eventually cause the wall of the aorta to rupture. Once the aorta ruptures, fatal hemorrhaging can occur very quickly. Repair of abdominal aortic aneurysms has typically required major abdominal surgery in which the diseased segment of the aorta is removed and replaced with a prosthetic device, such as a synthetic stent graft.

To repair the abdominal aortic aneurysm, the synthetic stent graft is delivered from the femoral or iliac artery to the aneurysm via a delivery catheter. The stent graft is then expanded to secure the stent graft within the aorta, and to define a passageway through the abnormally dilated section of the aorta to fluidly couple a healthy section of the aorta upstream of the aneurysm with one or more blood vessels downstream of the aneurysm. For example, if the abdominal aortic aneurysm occurs below the kidney area, then the surgeon generally must fluidly couple a portion of the aorta upstream of the aneurysm with portions of both of the iliac arteries downstream of the aneurysm to maintain bloodflow therebetween while excluding the abnormally dilated section of the aorta. The risks associated with repairing an abdominal aortic aneurysm are numerous, and the success of such procedures is dependent upon many variables, including the time required to complete the procedure, the type and quality of the stent grafts used, and the ability of the surgeon to accurately position the stent grafts in the patient.

SUMMARY OF THE INVENTION

The present invention is directed to an apparatus and method for repairing an aneurysm in the abdominal aorta of a patient. The apparatus includes first and second stent grafts which are attachable to each other, and a flexible guidewire detachably attached to the first stent graft.

The first stent graft is preferably made from a metal form structure in combination with a flexible fabric, and has an upper tubular body and a lower bifurcation. The upper tubular body defines an inlet, and the lower bifurcation includes a first tubular leg which defines a first outlet and a second tubular leg which defines a second outlet. The second tubular leg is shorter than the first tubular leg, and the first and second tubular legs are in fluid communication with the inlet of the upper tubular body. As discussed below, the guidewire is detachably attached at one end to the first stent graft at a location upstream of the lower bifurcation, and extends through the second tubular leg of the lower bifurcation.

The first stent graft is sufficiently collapsible and flexible to allow it to be inserted into a delivery catheter in a collapsed state for delivery to a location at and adjacent the aneurysm, and is expandable into an expanded configuration within the aorta and within a first of the two iliac arteries of the patient.

The second stent graft is also preferably made from a metal form structure in combination with a flexible fabric, and comprises a hollow elongated member which is sufficiently collapsible and flexible to allow it to be inserted into a catheter in a collapsed state for delivery through a second of the two iliac arteries, and for partial insertion into the second tubular leg of the first stent graft in the aorta downstream of the aneurysm. The second stent graft is expandable into an expanded configuration within the second tubular leg of the first stent graft and within the second iliac artery. The first and second stent grafts thus function in the patient to define passageways for bloodflow from a healthy section of the aorta upstream of the aneurysm to the common iliac arteries downstream of the aneurysm while excluding the damaged or otherwise unhealthy portion of the aorta as further discussed below.

As indicated above, the flexible guidewire is detachably attached to the first stent graft at a location upstream of the lower bifurcation (e.g., to an inner surface of the upper tubular body), and extends through the second tubular leg of the lower bifurcation. The guidewire is preferably 0.35 mm or less in diameter and at least 65 cm in length. In one embodiment, the guidewire includes a hook which permits detachable attachment to the upper tubular body of the first stent graft. In another embodiment, the upper tubular body of the first stent graft includes a lip, and the guidewire is detachably attached to the lip. In yet another embodiment, the guidewire is bonded at its distal end to the upper tubular body of the first stent graft. As further discussed below, the flexible guidewire is manipulatable by a surgeon from the first iliac artery to the second iliac artery, and functions as a guide for a guide catheter which is advanced over the flexible guidewire and into the second tubular leg of the first stent graft. The guide catheter is used to detach the flexible guide wire from the second tubular leg of the first stent graft, to guide removal of the flexible guide wire, and to guide a stiffer guide wire which is distally advanced into the second tubular leg of the first stent graft. The guide catheter is then removed and a second catheter delivery system is advanced over the stiffer guide wire through the second iliac artery and into the second tubular leg of the first stent graft within the aorta to facilitate delivery and deployment of the second stent graft therein.

Prior to introducing the first and second stent grafts and flexible guidewire into the patient, preparations for taking an angiogram of the aneurysm and the surrounding blood vessels are as follows. Incisions are made in the patient to expose and isolate both femoral arteries. A needle having a bore is inserted through one of the incisions into a first of the two femoral arteries. A thin guidewire is inserted through the incision via the bore of the needle into the first of the two femoral arteries and advanced through the first femoral artery, through the first iliac artery (which is a direct continuation of the first femoral artery), through a portion of the aorta, to a location in the approximate vicinity of the aneurysm in the aortic wall. A sheath is then connected at the site of arteriotomy in the first femoral artery and an angiogram catheter is inserted through the sheath and advanced into the abdominal aorta.

An angiogram is performed and measurements are taken to determine the distance from the aneurysm to the bifurcation (e.g., the location where the aorta branches into the two common iliac arteries).

After the angiogram is performed, the thin guide wire is replaced with a stiffer wire, and first and second stent grafts as described above and of appropriate length are chosen based upon the measurements taken during the angiogram. A first catheter delivery system is advanced over the stiffer guidewire through the first femoral and iliac arteries of the patient to a location beyond (e.g., upstream of) the aneurysm in the aorta. The first stent graft (with flexible guidewire detachably attached thereto) is advanced with the first catheter delivery system to a location traversing the aneurysm in the aorta. The first catheter delivery system is operated to deploy the first stent graft and attached guidewire, and is then withdrawn. Deployment causes the upper tubular body of the first stent graft to expand within the aorta, and the first outlet of the first tubular leg to expand within the first iliac artery.

Next, a guidewire engagement device useful for grasping or manipulating the flexible guidewire is inserted through the second incision in the patient and advanced distally through the second femoral and iliac arteries to the aorta. The engagement device is then used to grasp, pull, or otherwise manipulate the flexible guidewire out of the first iliac artery and retracted proximally through the second iliac and femoral arteries. The flexible guidewire is preferably long enough so that its proximal end can be pulled out through the second incision in the second femoral artery so that it can be grasped by the surgeon while a guide catheter is advanced over it as further discussed below.

At this point, the first stent graft is fixed within the aorta with the first tubular leg fluidly coupling a healthy section of aorta upstream of the aneurysm with the first iliac artery, and the second tubular leg is fully disposed within the aorta upstream of the second iliac artery. A guide catheter is advanced through the second incision and over the flexible guidewire, which is attached to the first stent graft. The flexible guidewire guides the guide catheter through the second femoral and iliac arteries, through a portion of the aorta, and into the second tubular leg of the first stent graft. It will be appreciated that the attachment of the flexible guidewire to the upper tubular body of the first stent graft and its extension through the second tubular leg makes it much easier for the surgeon to advance the guide catheter into the second tubular leg.

Once the guide catheter is disposed inside the second tubular leg of the first stent graft, the guide catheter delivery system is further advanced distally (upstream) to detach the flexible guidewire from the first stent graft (e.g., by applying a longitudinal pushing force against the attached distal end of the flexible guidewire). The flexible guidewire is then pulled proximally through the second tubular leg, the aorta, the second iliac and femoral arteries, and out of the patient through the second incision while the guide catheter remains advanced within the second tubular leg.

A stiffer guide wire is then introduced into the patient and advanced distally through the guide catheter to the distal end of the guide catheter. The guide catheter is then removed from the patient, and a second catheter delivery system provided with the second stent graft is distally advanced through the patient over the stiffer guide wire to the second tubular leg of the first stent graft. The second stent graft is then deployed from the second catheter delivery system into engagement with the second tubular leg of the first stent graft. It will be appreciated that the first and second stent grafts will now define passageways for bloodflow from the aorta upstream of the aneurysm to both of the common iliac arteries downstream of the aneurysm while excluding the damaged or otherwise unhealthy portion of the aorta. It will also be appreciated that this method of advancing and deploying the first and second stent grafts through the femoral, iliac, and aortic arteries may be used in other medical applications (e.g., medical applications in which other blood vessels include a target vessel and one or more branch vessels), and that bifurcated stent grafts having an attached guidewire may be used in other parts of the body besides the abdominal aorta.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
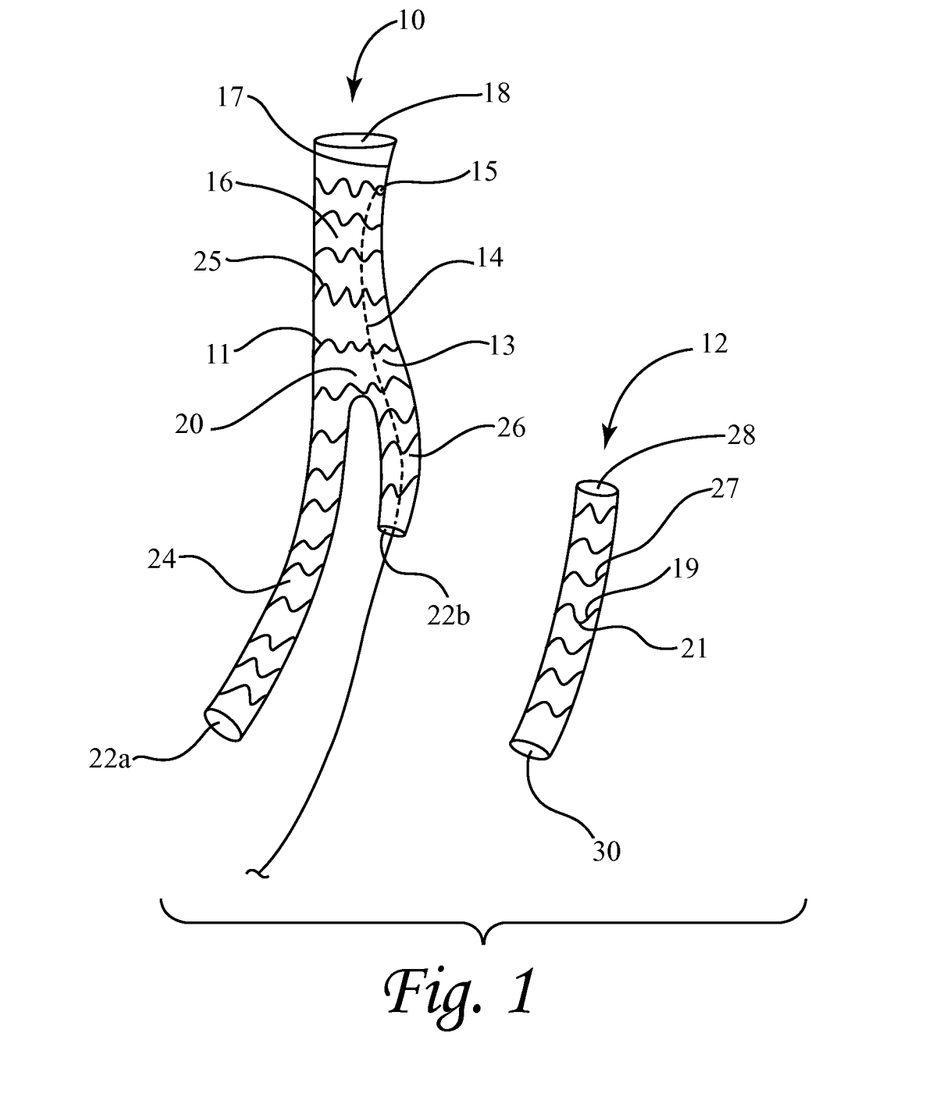
FIG. 1 is a schematic view of the first stent graft, the second stent graft, and the flexible guidewire in accordance with the present invention.

Turning now to FIG. 1, the invention includes a first stent graft 10, a second stent graft 12, and a flexible guidewire 14 for use in blood vessels of a patient. The first stent graft 10 has an upper tubular body 16 which defines a hollow inlet 18, and a lower bifurcation 20 which includes a first tubular leg 24 defining a first outlet 22a and a second tubular leg 26 which is shorter than the first tubular leg 24 and defines a second outlet 22b. The first and second tubular legs 24, 26 are in fluid communication with the hollow inlet 18. The first stent graft 10 is preferably made from at least one metal form structure 11, comprising struts 25, in combination with a flexible fabric 13.

The second stent member 12 is also preferably made from at least one metal form structure 19, comprising struts 27, in combination with a flexible fabric 21, and comprises a hollow elongated member having a single inlet 28 and a single outlet 30. The inlet 28 of the second stent member 12 is adapted to be insertable into the hollow second leg 26 of the first stent graft 10 inside the aorta of a patient as further discussed below.

The first and second stent grafts 10, 12 may be made from any materials known in the art which are suitable for advancement through the femoral, iliac, and aortic arteries of a patient, and for deployment in the iliac and aortic arteries. For the graft, such materials, for example, may be formed from a twill weave, non-crimped polyester, Gore-Tex®, Dacron® or equivalent biocompatible material. For the stents, materials such as super-elastic or heat activated nickel-titanium metal alloys may be used, which give them sufficient shape memory and/or bias to automatically expand them to an expanded configuration in the aortic and iliac arteries of a patient. Alternatively, the stent may comprise pressure expandable structured elements. The first and second stent grafts 10, 12 are therefore sufficiently collapsible and flexible to allow them to be inserted into a standard delivery catheter for delivery to and deployment at and adjacent an aneurysm in the aorta of a patient as further discussed below with respect to FIGS. 4-10.

The flexible guidewire 14 extends through the second tubular leg 26 and second outlet 22b of the lower bifurcation 20 of the first stent graft 10, and is detachably attached at an attachment end 15 to the first stent graft 10, preferably to an interior surface 17 of the upper tubular body 16. Glue may be used to form the attachment bond between the attachment end 15 and the interior surface 17 of the upper tubular body 16, and other adhesive materials known in the art may also be utilized, provided that the guidewire 14 is detachable from the upper tubular body 16 via a longitudinal force received at the attachment end 15 in vivo during a stent graft procedure, as further discussed below with respect to FIG. 8. The flexible guidewire 14 is preferably at least 65 cm in length and 0.35 mm or less in diameter.

Figures 2A, 2B:
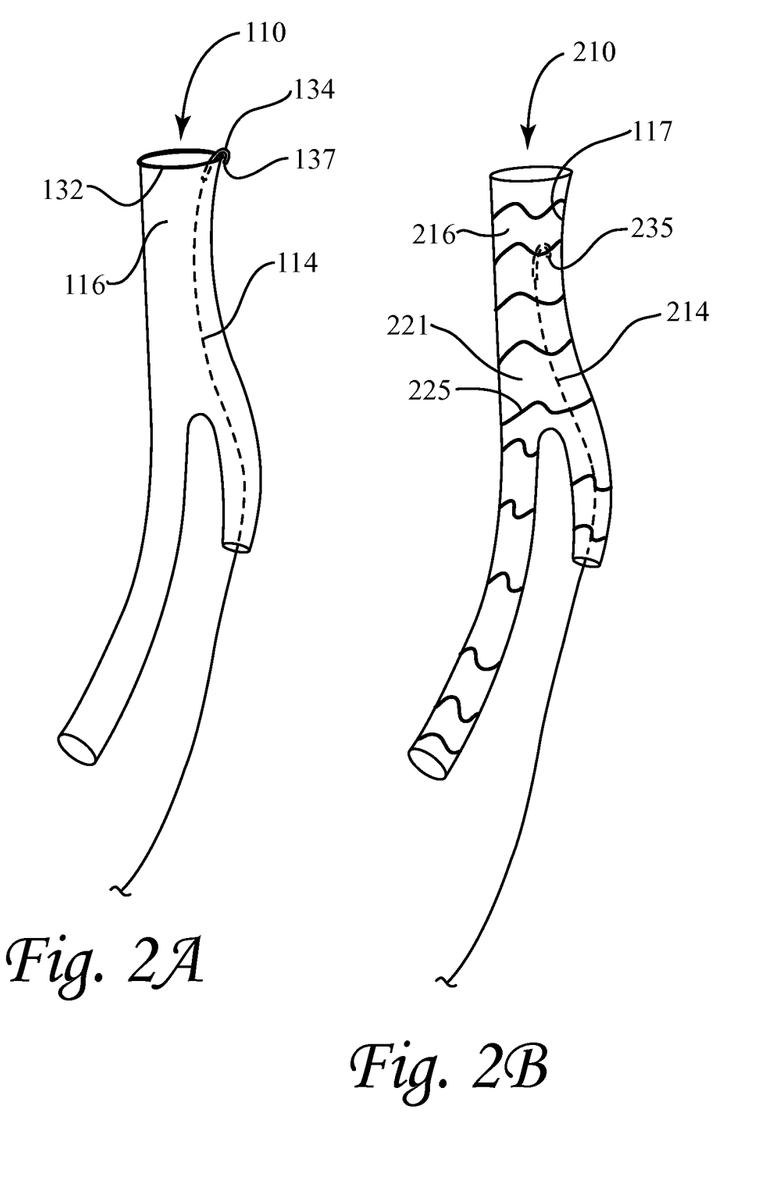
FIG. 2A is a schematic view of one embodiment of the invention in which the flexible guidewire is detachably attached to an upper rim of the first stent graft.
FIG. 2B is a schematic view of another embodiment of the invention in which the flexible guidewire has a hook which is detachably attached to a protrusion extending from an inner surface of the first stent graft.

Turning to FIG. 2A, one embodiment of the apparatus of the invention is shown in which an upper tubular body 116 of a first stent graft 110 according to the invention includes an upper rim 132 at one end of the first stent graft 110, and a guidewire 114 includes a hook 134 which is detachably attached to the upper rim 132. The hook 134 may be attached to the upper rim 132 with glue or other suitable adhesive, or may simply hook onto the upper rim 132. The hook 134 should be provided with a blunt tip 137 so as to not pierce the first stent member 110 during advancement through and deployment of the first stent member 110 in the patient.

Turning to FIG. 2B, another embodiment of the apparatus of the invention is shown in which an upper tubular body 216 of a first stent graft 210 includes an internal lip, shelf, or other protrusion 235 extending from an interior surface 117, and a guidewire 214 detachably attached to the protrusion 235 via glue, a hook, or other suitable fastener. Alternatively, the guidewire may be directly attached or tied to a strut 225 of the metal form structure stent portion of the stent graft 210 or tied to fabric 221 of the stent graft 210.

As further discussed below, once deployed within the patient with the first stent graft 10, the flexible guidewire 14, by virtue of being attached to the first stent graft 10, is manipulatable by a surgeon from the first iliac artery to the second iliac artery in the patient so that it can function to guide the advancement of a guide catheter through the second iliac artery and into the second tubular leg 26 of the first stent graft 10 in order to guide a stiffer guide wire which is distally advanced into the second tubular leg of the first stent graft. As further discussed below, the guide catheter is then removed and a second catheter delivery system is advanced over the stiffer guide wire through the second iliac artery and into the second tubular leg of the first stent graft within the aorta to facilitate delivery and deployment of the second stent graft therein.

Figure 3A:
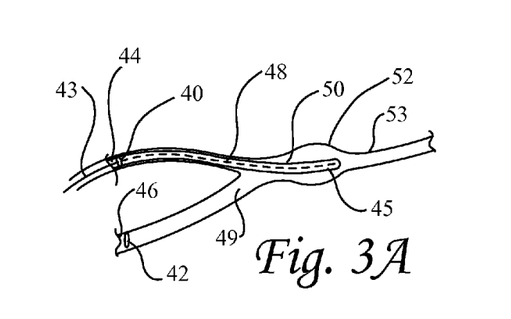
FIG. 3A is a schematic view of first and second iliac arteries and first and second femoral arteries in a patient, as well as an angiogram catheter.

Prior to introducing the first and second stent grafts 10, 12 and flexible guidewire 14 into the patient, preparations for taking and performing an angiogram of the aneurysm and the surrounding blood vessels are as follows. Turning to FIG. 3A, according to well-known techniques, the patient is anesthetized with all standard precautions. First and second incisions 40, 42 are made in the patient to expose first and second femoral arteries 44, 46. A needle (e.g. 9-11 French—not shown) having a bore is inserted through the first incision 40 into the first femoral artery 44. A thin guidewire 43 (e.g., a 0.35 mm Benson wire) is inserted through the first incision 40 via the bore of the needle into the first femoral artery 44 and advanced through the first femoral artery 44, through the first iliac artery 48 (which is a direct continuation of the first femoral artery 44), through a portion of the aorta 50, to a location in the approximate vicinity of the aneurysm 52 in the aortic wall 53. A sheath (e.g., 6 Fr—not shown) is then connected at the site of arteriotomy in the first femoral artery 44 and an angiogram catheter 45 (e.g., a 5 Fr. 65 cu/90 cm pig tail catheter) is inserted through the sheath and into the abdominal aorta. An angiogram is then performed and measurements are taken to determine the approximate distance from, for example, the aneurysm 52 to the bifurcation 56 where the aorta 50 branches into the first and second iliac arteries 48, 49, or the distance from the aneurysm 52 to each of the first and second iliac arteries 48, 49).

Figure 3B:
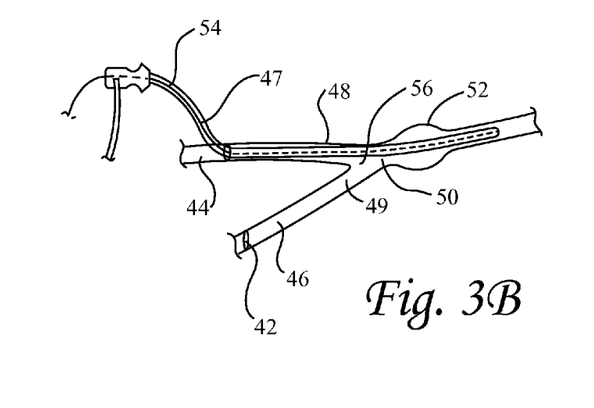
FIG. 3B is a schematic view of a delivery catheter advanced through the first femoral artery, the first iliac artery, and the aorta.

After performing the angiogram, the thin guidewire 43 is then proximally retracted from the patient through the first femoral and iliac arteries 44, 48 without retracting the catheter 45, and a stiffer guidewire 47 (e.g., a 260 cm/300 cm wire) (FIG. 3B) is advanced through the catheter 45 to the distal end of the catheter 45. The catheter 45 is then removed from the patient through the first femoral and iliac arteries 44, 48, and first and second stent grafts as described above and of appropriate length are chosen based upon the measurements taken during the angiogram.

Figure 4:
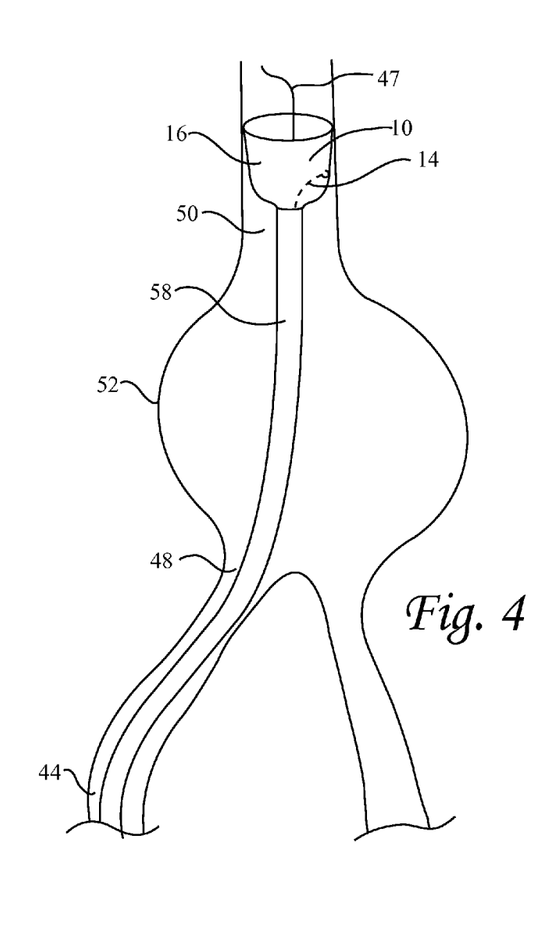
FIG. 4 is an enlarged schematic view of the aorta, iliac arteries, and delivery catheter of FIG. 3B with a portion of the first stent graft deployed within a healthy portion of the aorta.

Turning to FIG. 4, a first catheter delivery system 58 (preferably at least a 20 Fr. delivery system) provided with the first stent graft 10 is advanced over the stiffer guidewire 47 through the first femoral and first iliac arteries 44, 48 of the patient to a location beyond (e.g., upstream of) the aneurysm 52 in the aorta 50. The first stent graft 10 with flexible guidewire 14 detachably attached thereto is then deployed from the first catheter delivery system 58 to the location upstream of the aneurysm 52. The first catheter delivery system 58 may utilize any type of catheter and stent delivery device known in the art which are suitable for deployment in the abdominal aorta. For example, stent delivery devices are discussed in U.S. Pat. No. 7,594,926 to Linder, which is herein incorporated by reference in its entirety. As shown, during deployment from the first catheter delivery system 58, the stent graft 10 moves from a collapsed state within the first catheter delivery system 58 to an expanded state outside of the catheter delivery system 58 within the aorta 50.

Figure 5:
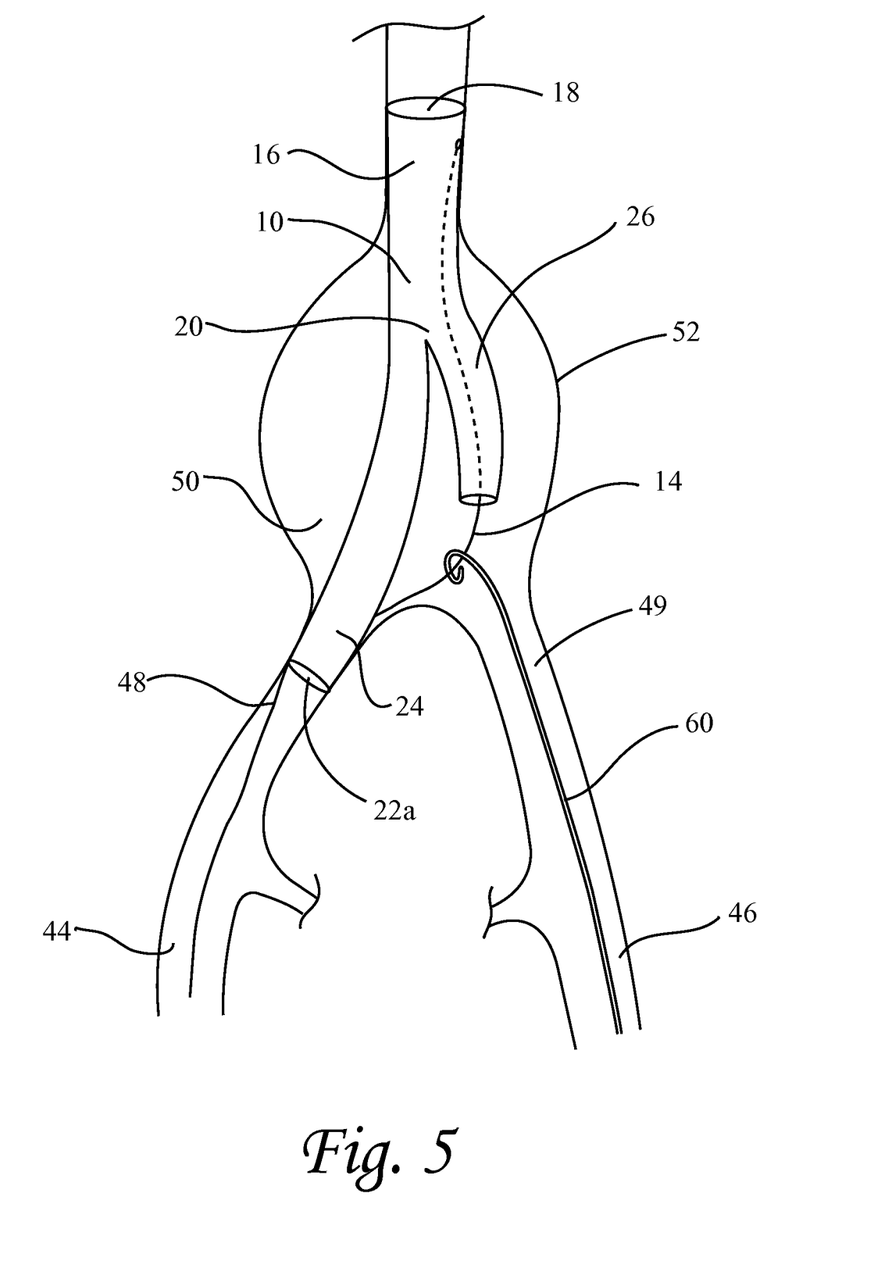
FIG. 5 is a schematic view of the aorta, iliac, and femoral arteries of FIG. 4 with the first stent graft fully deployed within both the aorta and the first iliac artery, the flexible guidewire extending through the second tubular leg of the first stent graft and the first iliac artery, and a guidewire engagement device disposed in the second iliac and second femoral arteries.

Turning to FIG. 5, the first catheter delivery system has been completely removed from the patient, leaving the first stent graft 10 and flexible guide wire 14 fully deployed with the hollow inlet 18 of the upper tubular body 16 positioned upstream of the aneurysm 52, the first tubular leg 24 of the lower bifurcation 20 expanded within both the aorta 50 and the first iliac artery 48 with the first outlet 22a positioned inside the first iliac artery 48, and the second tubular leg 26 expanded within the aorta 50.

A needle (not shown) is then inserted through the second incision 42 into the second femoral artery 46, and a sheath (not shown) is then connected at the site of arteriotomy in the second femoral artery 46. A snare, hook, pig-tail, clasp, or other guidewire engaging instrument 60 useful for grasping or manipulating the flexible guidewire 14 is inserted through the second incision 42 (FIG. 3A) via the bore of the needle through the sheath into the patient, and advanced distally through the second femoral and second iliac arteries 46, 49 to the aorta 50. As shown in FIG. 5, the flexible guidewire 14 extends at this point through the second tubular leg 26 of the first stent graft 10 toward and through the first iliac artery 48 and first femoral artery 44. The guidewire engaging instrument 60 is then used to snare, grasp, pull, or otherwise manipulate the flexible guidewire 14 out of the first iliac artery 48 and retract it proximally through the second iliac artery 49 and second femoral artery 46 by retracting the guidewire engaging instrument 60 proximally through the second iliac artery 49 and second femoral artery 46. The flexible guidewire 14 is preferably long enough so that its proximal end can be pulled out through the second incision 42 in the second femoral artery 46 and grasped by the surgeon while a guide catheter is distally advanced over it as further discussed below.

Figure 6:
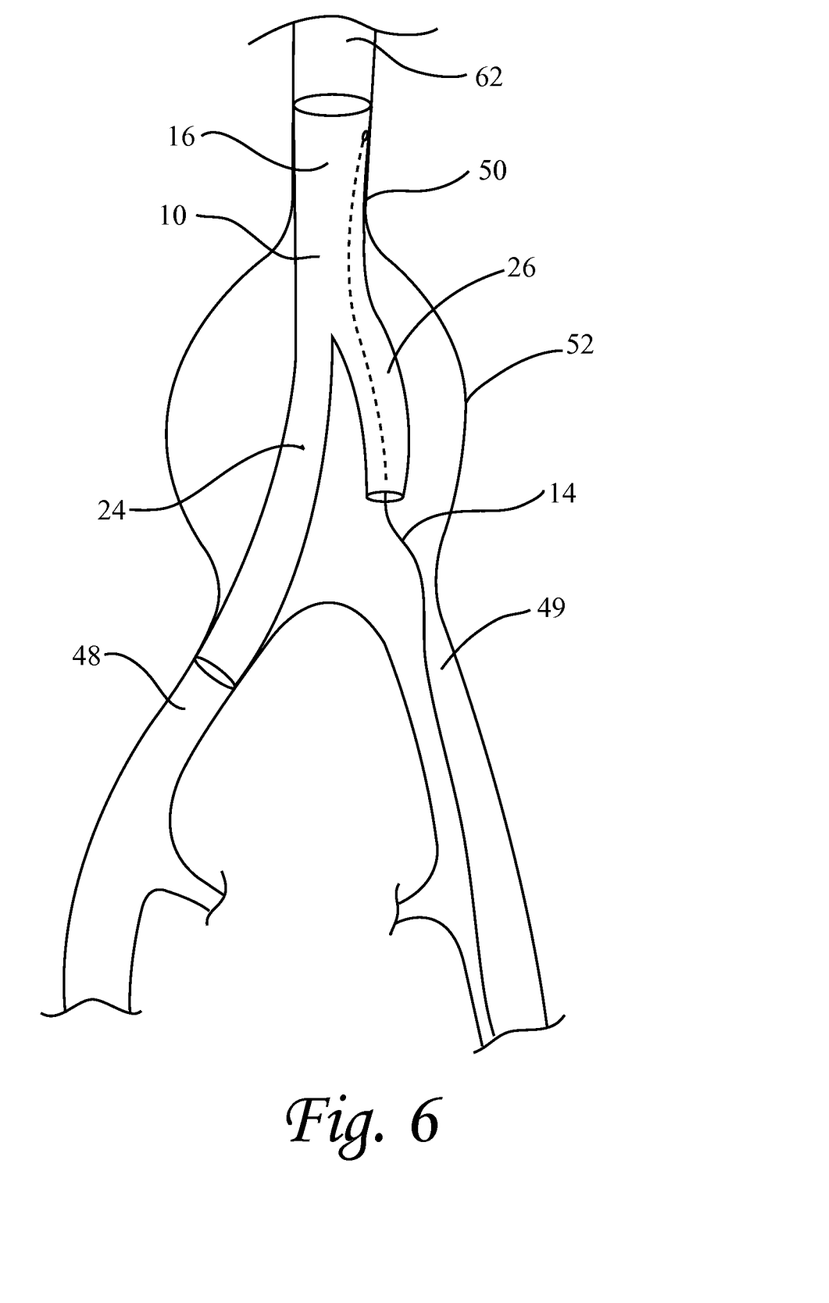
FIG. 6 is a schematic view of the aorta, iliac and femoral arteries, first stent graft, and flexible guidewire of FIG. 5 with the flexible guidewire extending through the second tubular leg of the first stent graft and the second iliac and second femoral arteries.

Turning now to FIG. 6, the first stent graft 10 is fixed within the aorta 50 with the first tubular leg 24 fluidly coupling a healthy section 62 of the aorta 50 upstream of the aneurysm 52 with the first iliac artery 48, with the second tubular leg 26 fully disposed within the aorta 50 upstream of the second iliac artery 49, and with the flexible guidewire 14 still attached to the upper tubular body 16 of the first stent graft 10 and now extending through both the second tubular leg 26 and the second iliac artery 49.

Figure 7:
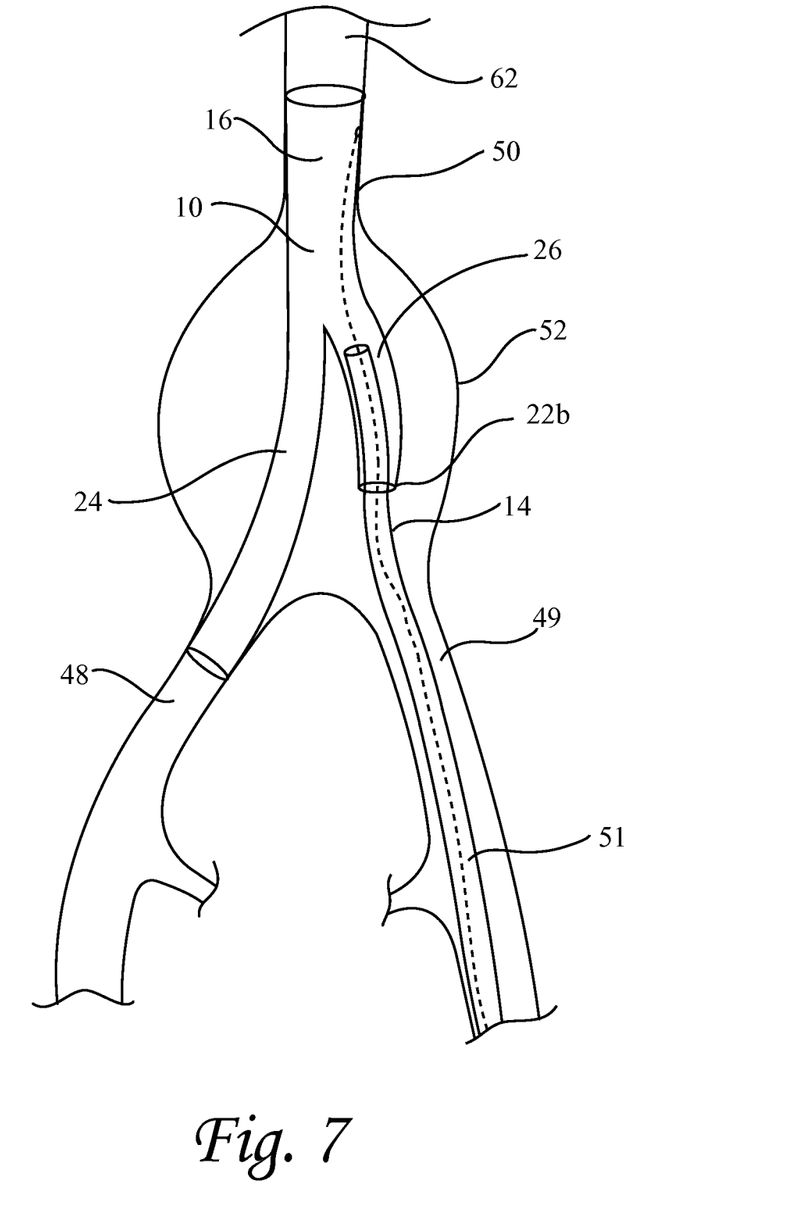
FIG. 7 is a schematic view of the aorta, iliac and femoral arteries, first stent graft, and flexible guidewire of FIG. 6, as well as a guide catheter advanced through the second femoral artery and second iliac artery over the flexible guidewire.

Turning to FIG. 7, a guide catheter 51 is advanced through the second incision 42 over the flexible guidewire 14. The flexible guidewire 14 guides the guide catheter 51 through the second femoral and iliac arteries 46, 49, through a portion of the aorta 50, and into the second tubular leg 26 of the first stent graft 10. It will be appreciated that the attachment of the flexible guidewire 14 to the upper tubular body 16 of the first stent graft 10 and its extension through the second tubular leg 26 will make it much easier for the surgeon to advance the guide catheter 51 into the second tubular leg 26 as the surgeon will not need to precisely position the guide catheter 51 in alignment with the second tubular leg 26 prior to distally advancing the guide catheter 51. Instead, the surgeon can simply advance the guide catheter 51 over the guidewire 14, and the guidewire 14 will guide the distal end of the guide catheter 51 into the second outlet 22b of the second tubular leg 26. Thus, the time for the surgeon to accomplish this critical step is reduced. In addition, it will be appreciated that the orientation of the second tubular leg 26 relative to the bifurcation 56 is rendered less important because it is not necessary for the surgeon to blindly guide a guidewire into the second tubular leg 26 prior to advancing the guide catheter 51.

Figure 8:
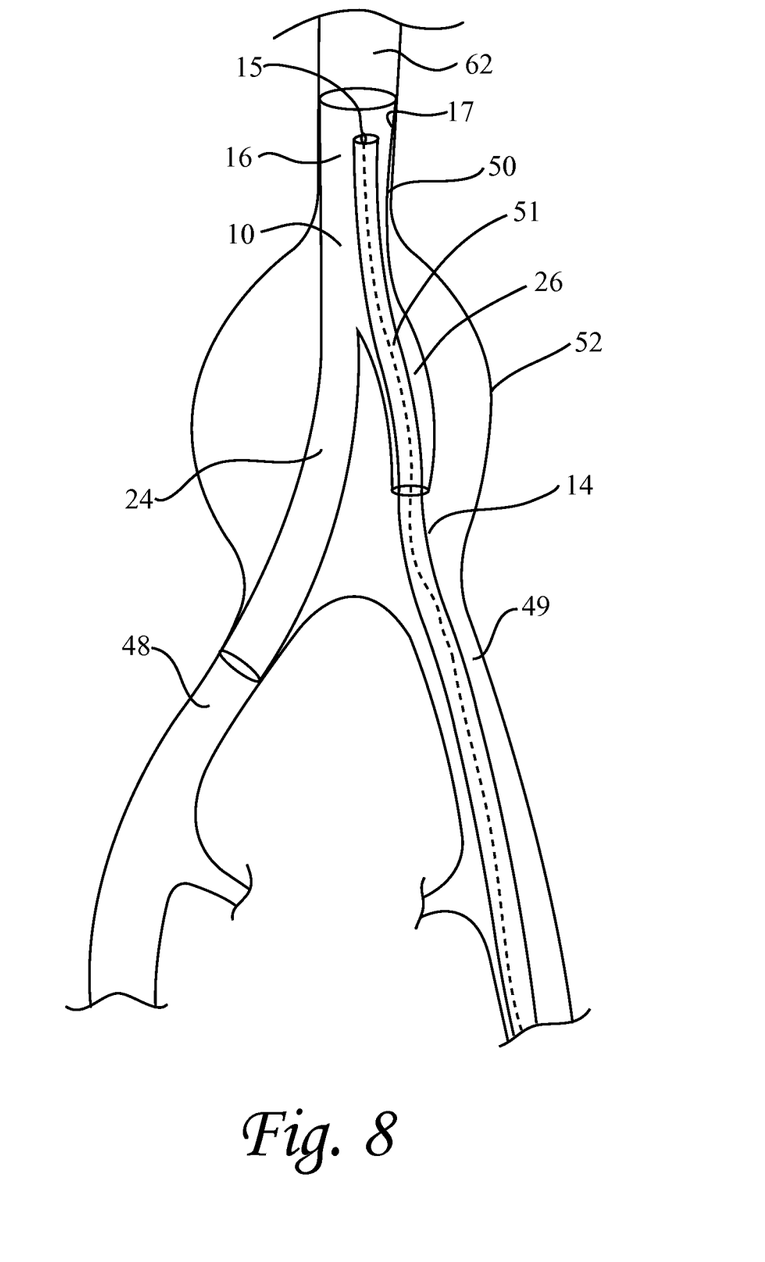
FIG. 8 is a schematic view of the aorta, iliac and femoral arteries, first stent graft, flexible guidewire, and guide catheter of FIG. 7 with the guide catheter advanced beyond the attachment end of the flexible guidewire and the guidewire detached from the first stent graft.

Turning to FIG. 8, once the guide catheter 51 is disposed inside the second tubular leg 26 of the first stent graft 10, the guide catheter 51 is further advanced distally (upstream) to detach the attachment end 15 of the flexible guidewire 14 from the interior surface 17 of the first stent graft 10 (e.g., by applying a longitudinal pushing force against the attachment end 15 of the flexible guidewire 14). As the upper tubular body 16 of the first stent graft 10 is wedged inside of the aorta 50, it is longitudinally fixed thereto, and thus will supply an equal and opposite longitudinal force to the bond between the attachment end 15 and the interior surface 17, causing sheer stress sufficient to break the bond (or to release the otherwise formed mechanical attachment between the flexible guidewire 14 and the first stent graft 10). It will be appreciated that the bond between the attachment end 15 and the first stent graft 10 should be strong enough to resist separation when the guide catheter 51 is initially placed in the patient and distally advanced through the second iliac artery 49 over the guidewire 14, but weak enough to separate when the distal end of the guide catheter 51 reaches the attachment end 15 and applies a longitudinal force thereto. If the attachment end 15 is hooked to an upper rim or shelf/protrusion extending from the interior surface 17 of the first stent graft 10 as discussed with respect to FIGS. 2A and 2B, then such upper rim, shelf, or protrusion is preferably made from material which will not break off of the interior surface 17 so that such material will not enter the bloodstream.

Once the flexible guidewire 14 is separated from the first stent graft 10, it is retracted proximally through the second tubular leg 26, the aorta 50, the second iliac and femoral arteries 49, 46, and out of the patient through the second incision 42 while the guide catheter 51 remains advanced within the second tubular leg 26. At this point, it will be appreciated that locational access to the second tubular leg 26 is provided for any desired use. By way of example, an angiogram may be conducted. Also, a stiffer guide wire 55 (FIG. 9) may then be advanced through the guide catheter 51 to the distal end of the guide catheter 51 inside the second tubular leg 26, and the guide catheter 51 may be removed, leaving the stiffer guide wire 55 in place.

Figure 9:
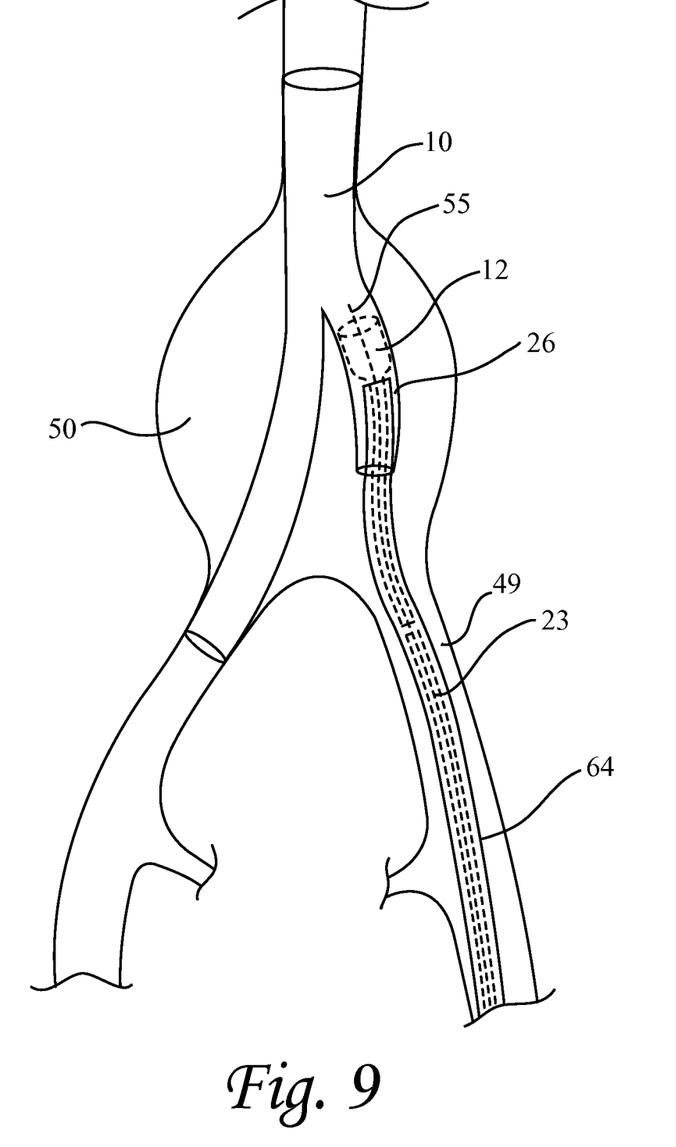
FIG. 9 is a schematic view of the aorta, iliac and femoral arteries, first stent graft, stiffer guide wire, and second delivery catheter and stent delivery device with a portion of the second stent graft deployed from the second delivery catheter and expanded within the second tubular leg of the first stent graft.

Turning to FIG. 9, with the stiffer guide wire 55 in place, a second catheter delivery system 64 (preferably at least 20 Fr.) may be provided with the second stent graft 12 and a stent delivery device 23 and may be introduced into the patient through the second incision 42 and distally advanced over the stiffer guide wire 55, which guides the second catheter delivery system 64 through the second femoral and illiac arteries 56, 49 and aorta 50, and into the second tubular leg 26 of the first stent graft 10.

Figure 10:
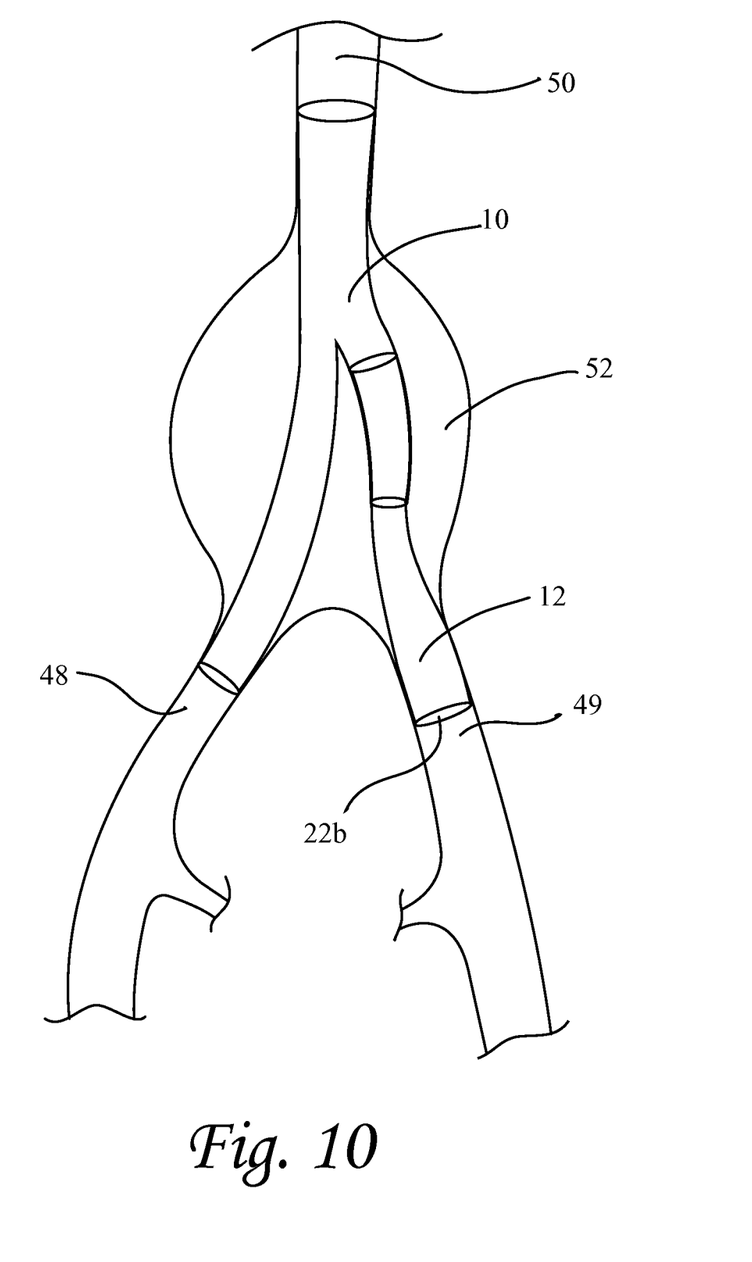
FIG. 10 is a schematic view of the aorta, iliac and femoral arteries, and first and second stent grafts of FIG. 9 with the second stent graft fully deployed and extending within the second tubular leg of the first stent graft, the aorta, and the second iliac artery.

The second stent graft 12 can then be deployed from the second catheter delivery system 64 inside the second tubular leg 26 of the first stent graft 10 (e.g., the delivery catheter is refracted proximally relative to the stent delivery device 23, which is held longitudinally fixed, which deploys the second stent graft 12). The stiffer guide wire 55 may be removed from the patient before or after deployment of the second stent graft 12. The second catheter delivery system 64 can be operated to deploy the second stent graft 12 between the hollow second leg 26 and the second iliac artery 49 such that the second outlet 22b is positioned within the second iliac artery 49 as shown in FIG. 10.

It will be appreciated that the first and second stent grafts 10, 12 will now define passageways for bloodflow from the aorta 50 upstream of the aneurysm 52 to both of the common iliac arteries 48, 49 downstream of the aneurysm 52 while excluding the damaged or otherwise unhealthy portion (e.g., the aneurysm 52) of the aorta 50. Additional stent grafts may be applied to one or more blood vessels as needed.

There have been described and illustrated herein several embodiments of an apparatus and a method of repairing abdominal aortic aneurysms. While particular embodiments of the invention have been described, it is not intended that the invention be limited thereto, as it is intended that the invention be as broad in scope as the art will allow and that the specification be read likewise. Thus, while particular shaped and sized stent grafts have been disclosed, it will be appreciated that other shapes and sizes may be used as well. While first and second stent grafts having a metal form structure in combination with a flexible fabric have been disclosed, it will be appreciated that other materials may be used to form the first and second stent grafts. In addition, while particular types of adhesives have been disclosed, it will be understood that other adhesives and fasteners can be used. Also, while a bifurcated first stent graft and an elongate second stent graft have been disclosed, it will be recognized that additional stent grafts can be attached to the respective ends of the first and second stent grafts, and/or to additional blood vessels as needed. For example, it will be appreciated that extension stent grafts may be added to the upstream end of the first stent graft and to the downstream end of the second stent graft, and that stent grafts with attached guidewires may be used for other medical applications. While a particular catheter delivery system for delivering and deploying a stent graft has been disclosed, it will be appreciated that other catheter delivery systems for delivering and deploying stent grafts known in the art may be employed. Furthermore, while a particular method has been disclosed, it will be understood that a number of steps of the method of the invention may be eliminated or modified as needed, and that the method may be used for bifurcated stent grafts applicable to other medical procedures in which a catheter needs to be guided into a specific leg of the bifurcated stent. It will also be appreciated that while a method for repairing an aneurysm in the aorta of a patient has been disclosed, the method may be modified and utilized to repair an aneurysim in another blood vessel of the patient, such as, for example, an aneurysim in the iliac artery of a patient. It will therefore be appreciated by those skilled in the art that yet other modifications could be made to the provided invention without deviating from its spirit and scope as claimed.

What is claimed is:

1. A method for repair of an aneurysm in a patient in which first and second iliac arteries branch off of an aorta which includes the aneurysm, the method comprising:
    obtaining a first catheter delivery system provided with a first stent graft having an upper tubular body, a lower bifurcation, and a flexible guidewire, the upper tubular body defining an inlet, the lower bifurcation including a first tubular leg defining a first outlet and a second tubular leg defining a second outlet, the flexible guidewire having an attachment end detachably attached to the upper tubular body and the flexible guidewire extending through the second tubular leg of the lower bifurcation;
    advancing said first catheter delivery system with said attachment end of said flexible guidewire attached to the upper tubular body through the first iliac artery of the patient to a location upstream of the aneurysm in the aorta, such that the attachment end of the flexible guidewire moves together the upper tubular body;
    deploying the first stent graft with the inlet positioned in the aorta upstream of the aneurysm, the first outlet of the first tubular leg positioned in the first iliac artery downstream of the aneurysm, and the second outlet of the second tubular leg positioned at or adjacent the aneurysm;
    advancing a guidewire engagement device distally through the second iliac artery to the flexible guidewire and while the attachment end of the flexible guidewire is attached to the first stent graft, pulling the flexible guidewire out of the first iliac artery and into the second iliac artery;
    advancing a guide catheter over the flexible guidewire to the second tubular leg of the first stent graft while the attachment end of the flexible guidewire is attached to the first stent graft;
    detaching the attachment end of the flexible guidewire from the first stent graft and removing the flexible guidewire from the first stent graft and the second iliac artery;
    introducing a stiffer guide wire through the guide catheter to the second tubular leg of the first stent graft;
    removing the guide catheter from the patient;
    advancing a second catheter delivery system provided with a second stent graft over the stiffer guide wire, the second stent graft defining an inlet and an outlet;
    deploying the second stent graft with the inlet of the second stent graft inside of the second tubular leg of the first stent graft and the outlet of the second stent graft positioned within the second iliac artery downstream of the aneurysm.

2. A method according to claim 1, wherein:
said detaching the attachment end of the flexible guidewire from the first stent graft comprises using the guide catheter.

3. A method according to claim 1, further comprising:
prior to advancing the second catheter delivery system provided with the second stent graft, measuring an approximate distance between the aneurysm and at least one of the first and second iliac arteries.

4. A method according to claim 1, wherein:
prior to deploying the first stent graft, performing an angiogram of the first and second illiac arteries and the aorta.

5. A method according to claim 1, wherein:
the guidewire has a length and a diameter, the diameter is no more than 0.35 mm, and the length is at least 65 cm.

6. A method for repair of an aneurysm in a target blood vessel of a patient in which first and second blood vessels branch off of the target blood vessel, the method comprising:
    obtaining a catheter delivery system provided with a first stent graft having an upper tubular body, a lower bifurcation, and a flexible guidewire, the upper tubular body defining an inlet, the lower bifurcation including a first tubular leg defining a first outlet and a second tubular leg defining a second outlet, the flexible guidewire having an attachment end detachably attached to the upper tubular body and the flexible guidewire extending through the second tubular leg of the lower bifurcation;
    advancing the catheter delivery system with the attachment end of the flexible guidewire attached to the upper tubular body through the first blood vessel of the patient to a location upstream of the aneurysm in the target blood vessel, such that the attachment end of the flexible guidewire moves together the upper tubular body;
    deploying the first stent graft with the inlet positioned in the target blood vessel upstream of the aneurysm, the first outlet of the first tubular leg positioned in the first blood vessel downstream of the aneurysm, and the second outlet of the second tubular leg positioned at or adjacent the aneurysm;
    advancing a guidewire engagement device distally through the second blood vessel to the flexible guidewire and while the attachment end of the flexible guidewire is attached to the upper tubular body pulling the flexible guidewire out of the first blood vessel and into the second blood vessel; and
    advancing a catheter over the flexible guidewire through the second tubular leg of the first stent graft and into the upper tubular body, and using the catheter to detach the flexible guidewire from the first stent graft; and
    removing the flexible guidewire from the patient.

7. A method according to claim 6, further comprising:
deploying a second stent graft within the second tubular leg of the first stent graft and within the second blood vessel downstream of the aneurysm.

* * * * *